United States Patent [19]

Bercu

[11] Patent Number: 5,065,747

[45] Date of Patent: * Nov. 19, 1991

[54] METHOD FOR IMPROVING THE ACCURACY OF DIAGNOSIS OF GROWTH HORMONE DEFICIENCY

[75] Inventor: Barry B. Bercu, Tampa, Fla.

[73] Assignee: University of South Florida, Tampa, Fla.

[*] Notice: The portion of the term of this patent subsequent to Jul. 4, 2006 has been disclaimed.

[21] Appl. No.: 439,407

[22] Filed: Nov. 21, 1989

[51] Int. Cl.$^5$ .................................................. A61B 5/00
[52] U.S. Cl. ..................................... 128/630; 128/632; 424/9; 604/49
[58] Field of Search ................... 604/49, 51; 128/630, 128/632; 424/9; 514/171; 530/311

[56] References Cited

U.S. PATENT DOCUMENTS

| | | | |
|---|---|---|---|
| 4,230,617 | 10/1980 | Sarantakis | 530/311 |
| 4,261,885 | 4/1981 | Sakakibara et al. | 530/311 |
| 4,410,512 | 10/1983 | Bowers | 514/17 |
| 4,727,041 | 2/1988 | Aroonsakal | 436/8 |
| 4,747,825 | 5/1986 | Linkie et al. | 604/51 |
| 4,844,096 | 7/1989 | Berco | 128/630 |

Primary Examiner—C. Fred Rosenbaum
Assistant Examiner—Mark O. Polutta
Attorney, Agent, or Firm—Joseph C. Mason, Jr.; Ronald E. Smith

[57] ABSTRACT

Somatostatin, a growth hormone suppressant, is administered to an individual before the growth hormone secretion of that individual is provoked. The somatostatin is applied first in bolus form and the bolus administration is followed by a prolonged adminstration of the somatostatin. Both the bolus and the subsequent administration of growth hormone suppressant can be administered intravenously. This procedure insures that the growth hormone secretion of the individual's pituitary gland will be reduced to a minimum, thereby insuring that the results of subsequent provocative tests will be standardized and thus interpreted more consistently.

14 Claims, No Drawings

METHOD FOR IMPROVING THE ACCURACY OF DIAGNOSIS OF GROWTH HORMONE DEFICIENCY

TECHNICAL FIELD

This invention relates, generally, to diagnostic methods. More particularly, it relates to a method whereby the diagnosis of growth hormone deficiency is improved.

BACKGROUND ART

Human growth normally occurs, in simplified terms, as a result of growth hormone secretion by the pituitary gland. In less simplified terms, growth occurs as a result of a complex interplay of factors. Accordingly, when a child is observed to be of unusually short stature for his or her age and a growth hormone deficiency is suspected, it is the current practice to administer various drugs to the child in an effort to provoke secretion of growth hormone. Normally, at least two provocative tests are administered; if the peak growth hormone response is less than 10 ng/mL after each administration of provocative drugs, then a diagnosis of growth hormone deficiency is usually made.

However, growth hormone secretion occurs in pulsatile or episodic patterns, i.e., at any given time a measurement of growth hormone secretion is likely to be very low, even in individuals not suffering from growth hormone deficiency, because such a measurement is highly likely to be taken between pulses.

Those suffering from a growth hormone deficiency may be misdiagnosed if a reading of growth hormone secretion is taken during a secretory pulse, i.e., the level of growth hormone may seem normal but such apparent normality may be attributable merely to the fact that growth hormone secretion was checked at its peak. Where growth hormone secretion is being checked after the administration of a provocative drug, it is important for the physician to know what amount of secretion is a result of the provocation, and what amount would have been secreted even in the absence of provocation.

The physician has no means for determining whether or not a particular patient is undergoing a secretory pulse at the time a reading is made. Just as importantly, a pulse may be beginning or ending when the reading is made, thereby producing skewed results that can lead to a misdiagnosis.

The art has dealt with this problem by taking multiple tests, in the hope that the physician will be able to make a meaningful interpretation of the test results if there is a large body of data to interpret.

The present technique is subject to many pitfalls and there is a need for a more reliable diagnostic method. However, the prior art, taken as a whole, neither teaches nor suggests how the present procedure could be improved.

DISCLOSURE OF INVENTION

Somatostatin is applied to patients suspected of having growth hormone deficiency prior to the administration of provocative tests. Since somatostatin is a growth hormone suppressant, this unique procedure insures that the patient will be in a growth hormone secretory trough before the provocative test is applied and thus the results of the provocative tests will be standardized and said results can be interpreted in a uniform manner.

It is the primary object of this invention to advance the art of growth hormone deficiency diagnosis by providing a new method that insures the patients are in a growth hormone secretory trough at the time a provocative test is applied.

Additional objects and advantages of this invention will become apparent to those skilled in the art as this description proceeds. The invention is new, useful and was not obvious to those of ordinary skill in the art at the time it was made.

BEST MODE FOR CARRYING OUT THE INVENTION

Somatostatin is administered to an individual in predetermined amounts at a predetermined rate before beginning a provocative test to insure that the individual's growth hormone secretion is at a minimum, i.e., fully suppressed, prior to the stimulation. In this manner, the chance that the individual's growth hormone secretion might be on an upslope, peak or downslope at the time of the stimulation is eliminated and a possible misdiagnosis is avoided. Importantly, the results of the provocative tests will be more standardized and thus more amenable to interpretation.

After the somatostatin has been administered, a growth hormone releasing factor (GRF) test may be conducted; the test reveals information about pituitary growth hormone reserve. More significantly, the somatostatin can be given prior to any provocative test, not just a GRF test.

Typical provocative tests of the type that would follow the administration of somatostatin include aerobic exercise, insulin-induced hypoglycemia, and the drugs clonidine, L-dopa, arginine and glucagon. The drugs may be administered sequentially and with an adjunctive drug such as estrogen and propranolol. L-tryptophan, Antilirium and valproic acid are other provocative testing drugs used by the present inventor. The hypothalamus has receptors for, or is otherwise acted upon by these drugs and the products of insulin-induced hypoglycemia and aerobic exercise. Once received by the hypothalamus, these drugs cause the hypothalamus to provoke the pituitary to either begin producing growth hormone releasing factor or to begin suppressing somatostatin. In other words, these drugs, induced hypoglycemia and/or exercise, with the possible exception of L-dopa, do not directly affect the pituitary, as those of ordinary skill in this art will appreciate. Another disclosure by the present inventor, U.S. Ser. No. 07/437,041, (copending) employs growth hormone releasing factor in the provocative test; said growth hormone releasing factor acts directly on the pituitary, as those of ordinary skill in this art well know.

An exemplary somatostatin pretreatment is as follows: 3.6 ug/kg intravenous bolus followed by 7.2 ug/kg/hr intravenous for up to 1-3 hours. The somatostatin may be given for longer periods of time but such longer periods are inconvenient in outpatient situations.

This somatostatin pretreatment insures that the individual's growth hormone secretion will be in a trough because somatostatin is a well known suppressant of growth hormone secretion. By initiating the provocative tests only after the trough has been definitely established in accordance with this disclosure, the results of the provocative tests will be more standardized and therefore can be interpreted with more assurance.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A method for improving the diagnosis of individuals having growth hormone deficiency, comprising the steps of administering to the individual a predetermined amount of somatostatin for a predetermined amount of time at a predetermined rate to establish a definite growth hormone secretory trough and following said step with a provocative test, said provocative test being of the type that acts on the hypothalamus and causes it to provoke the pituitary to produce growth hormone.

2. The method of claim 1, wherein the growth somatostatin is initially administered in bolus form and wherein said bolus administration is followed by an administration of said suppressant in a predetermined amount at a predetermined rate over a predetermined period of time.

3. The method of claim 2, wherein about 3.6 ug/kg of said somatostatin is administered in bolus form.

4. The method of claim 3, wherein said bolus is administered intravenously.

5. The method of claim 4, wherein said predetermined rate of said administration of somatostatin is about 7.2 ug/kg/hr.

6. The method of claim 5, wherein said provocative test includes aerobic exercise.

7. The method of claim 5, wherein said provocative test includes insulin-induced hypoglycemia.

8. The method of claim 5, wherein said provocative test includes clonidine.

9. The method of claim 5, wherein said provocative test includes L-dopa.

10. The method of claim 5, wherein said provocative test includes arginine.

11. The method of claim 5, wherein said provocative test includes glucagon.

12. The method of claim 5, wherein said provocative test includes L-tryptophan.

13. The method of claim 5, wherein said provocative test includes Antilirium.

14. The method of claim 5, wherein said provocative test includes valproic acid.

* * * * *